US012721991B2

(12) United States Patent
Huk

(10) Patent No.: US 12,721,991 B2
(45) Date of Patent: Sep. 1, 2026

(54) CASSETTE WITH FREE FLOW PREVENTION FOR INFUSION PUMP

(71) Applicant: B. Braun Medical Inc., Bethlehem, PA (US)

(72) Inventor: Michael Huk, Lehighton, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 642 days.

(21) Appl. No.: 18/129,223

(22) Filed: Mar. 31, 2023

(65) Prior Publication Data

US 2024/0325629 A1 Oct. 3, 2024

(51) Int. Cl.
*A61M 39/28* (2006.01)

(52) U.S. Cl.
CPC ....... *A61M 39/281* (2013.01); *A61M 2205/33* (2013.01)

(58) Field of Classification Search
CPC .......... A61M 5/16813; A61M 2205/12; A61M 2205/121; A61M 2205/128; A61M 39/28; A61M 39/281; A61M 39/284
See application file for complete search history.

(56) References Cited

U.S. PATENT DOCUMENTS

| | | | | |
|---|---|---|---|---|
| 5,551,850 | A | 9/1996 | Williamson et al. | |
| 5,658,133 | A * | 8/1997 | Anderson | A61M 5/172 73/19.1 |
| 5,807,075 | A | 9/1998 | Jacobsen et al. | |
| 6,231,320 | B1 | 5/2001 | Lawless et al. | |
| 7,285,111 | B2 | 10/2007 | Gaster | |
| 7,766,863 | B2 | 8/2010 | Gillespie et al. | |
| 8,888,738 | B2 | 11/2014 | Gillespie et al. | |
| 9,514,518 | B2 | 12/2016 | Gillespie et al. | |
| 9,937,289 | B2 | 4/2018 | Gillespie et al. | |
| 2013/0267899 | A1 | 10/2013 | Robert et al. | |
| 2018/0050153 | A1* | 2/2018 | Azapagic | A61M 5/14228 |
| 2020/0179592 | A1* | 6/2020 | Adams | A61M 5/168 |
| 2021/0146044 | A1* | 5/2021 | Burnard | F04B 43/12 |
| 2021/0290843 | A1 | 9/2021 | Hochman et al. | |
| 2022/0040405 | A1* | 2/2022 | Shoham | A61M 5/16813 |

FOREIGN PATENT DOCUMENTS

| | | | |
|---|---|---|---|
| EP | 1557187 | A1 | 7/2005 |
| WO | 2018204789 | A1 | 11/2018 |

OTHER PUBLICATIONS

International Search Report and Written Opinion for International Application No. PCT/US2024/017237, dated Jun. 17, 2024 (Jun. 17, 2024)—11 pages.

* cited by examiner

*Primary Examiner* — Andrew H Nguyen
(74) *Attorney, Agent, or Firm* — CM Law; Stephen J. Weed

(57) ABSTRACT

A cassette with free flow prevention for use with an ambulatory pump. The cassette includes a free flow prevention clamp and a housing. The free flow prevention clamp includes a clamping section having a first clamp side and a second clamp side. The housing supports the free flow prevention clamp and defines a channel for receiving a tube. The first and second clamp sides extend parallel to the channel and the clamping section extends across the channel. The free flow prevention clamp is configurable within the housing via an actuator assembly in an open condition that allows fluid flow through the tube when force is applied to the clamping section and in a closed condition that prevents fluid flow through the tube when the force is removed from the clamping section.

16 Claims, 8 Drawing Sheets

CASSETTE WITH FREE FLOW PREVENTION FOR INFUSION PUMP

FIELD OF THE INVENTION

The present disclosure is related to infusion pumps and, more particularly, to a cassette for use with an infusion pump that includes a free flow prevention device.

BACKGROUND

Infusion pumps deliver controlled doses of fluids such as medications, analgesics, and nutrition to patients. Infusion pumps are particularly well suited to delivering controlled doses of fluids over long periods of time, e.g., several hours or days. While many infusion pumps are designed for bedside use, there are ambulatory versions available. Ambulatory infusion pumps allow a patient to move around while the infusion pump is in use. This is beneficial for patients who would otherwise be confined to a bed, and it can help patients get some light exercise by walking or stretching. This also allows fluids to be delivered while patients are being transferred.

There are two conventional types of infusion pumps, syringe pumps that depress a syringe to deliver fluid from the syringe to a patient, and peristaltic pumps that act on a tube to control the rate of fluid flow through the tube from a bottle or bag of fluid to a patient. A concern with peristaltic pumps is that the force of gravity may cause an unintentional flow of fluid from the bottle or bag of fluid through the tube to the patient, which is commonly referred to as free flow.

SUMMARY

Examples described herein are directed to a cassette for use with an ambulatory pump. The cassette includes a free flow prevention clamp and a housing. The free flow prevention clamp includes a clamping section having a first clamp side and a second clamp side. The housing supports the free flow prevention clamp and defines a channel for receiving a tube. The first and second clamp sides extend parallel to the channel and the clamping section extends across the channel. The free flow prevention clamp is configurable within the housing via an actuator assembly in an open condition that allows fluid flow through the tube when force is applied to one of the clamp sides and in a closed condition that prevents fluid flow through the tube when the force is removed from at least one of the first or second clamp sides.

BRIEF DESCRIPTION OF THE DRAWINGS

The drawing figures depict multiple views of one or more implementations, by way of example only, not by way of limitations. In the figures, like reference numerals refer to the same or similar elements. The same numeral is used to represent the same or similar element across the multiple views. If multiple elements of the same or similar type are present, a letter may be used to distinguish between the multiple elements. When the multiple elements are referred to collectively or a non-specific one of the multiple elements is being referenced, the letter designation may be dropped.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and circuitry have been described at a relatively high-level, without detail, in order to avoid unnecessarily obscuring aspects of the present teachings.

Figure 1:
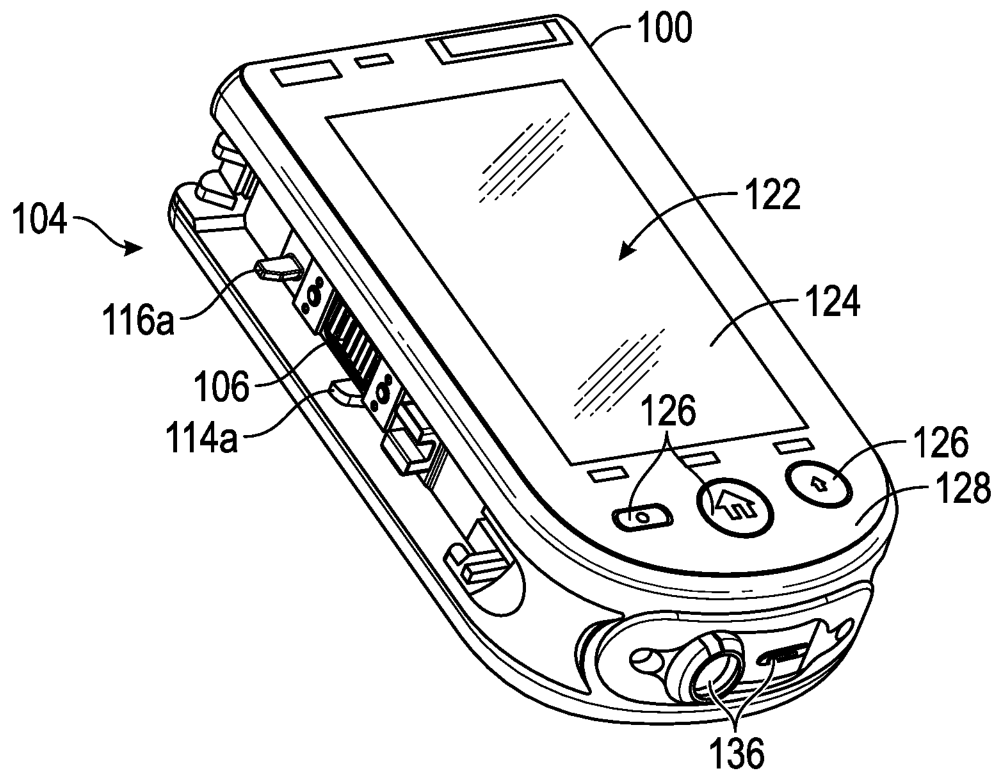
FIG. 1 is a perspective view of an example ambulatory infusion pump.
Figure 2:
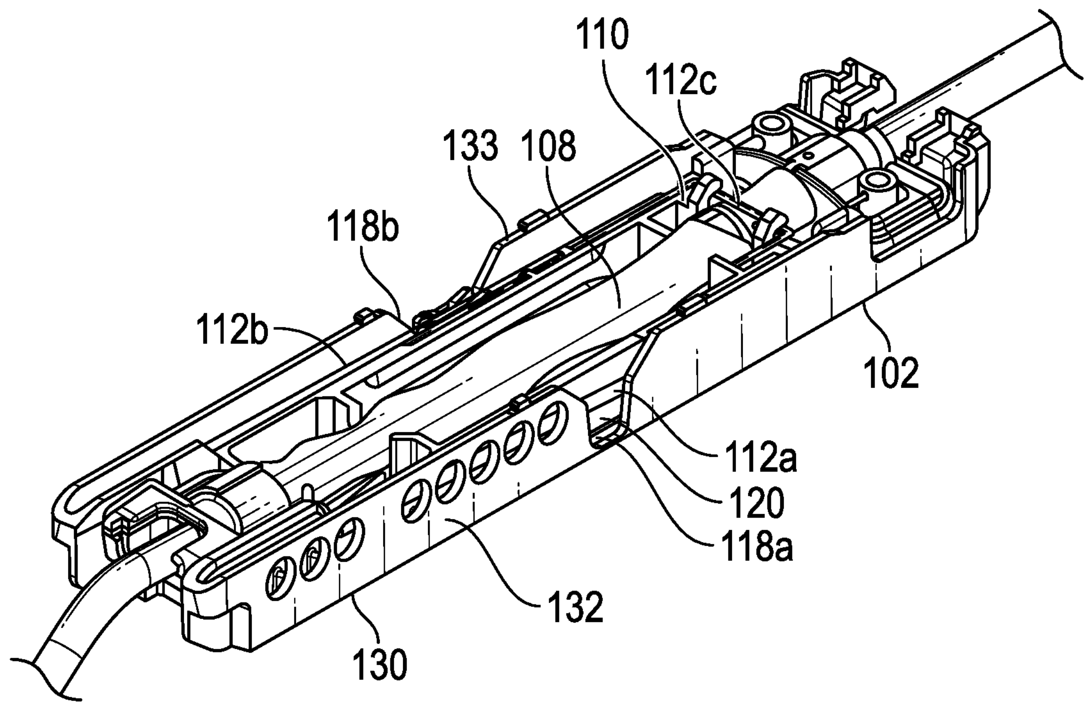
FIG. 2 is a perspective view of an example cassette with a free flow prevention clamp for use with the ambulatory pump of FIG. 1.

FIG. 1 depicts an example ambulatory pump or pump body 100 and FIG. 2 depicts an example cassette 102 with free flow prevention for use with the ambulatory pump 100. The ambulatory pump 100 includes a receptacle 104 configured to receive the cassette 102. A peristaltic pump 106 within the receptacle 104 acts upon a tube 108 extending through a channel within the cassette 102 to pump fluid from a fluid container (e.g., a bag or a bottle; not shown) into a patient. An example free flow prevention clamp 110 is positioned within the cassette 102 to allow fluid flow through the tube 108 when the cassette is coupled to the ambulatory pump 100 within the receptacle 104 (during which time the peristaltic pump 106 controls fluid flow through the tube 108) and to selectively cut off fluid flow through the tube 108 when the cassette 102 is not coupled to the ambulatory pump 100 in order to prevent unintentional fluid flow through the tube (e.g., free flow).

The ambulatory pump 100 includes a user interface for interacting with the ambulatory pump 100. The illustrated user interface includes a display (which may be a touchscreen) and buttons 126. A user controls operation of the ambulatory pump via the user interface. The ambulatory pump 100 additionally includes a housing 130 for containing and supporting the components of the ambulatory pump 100 such as the peristaltic pump 106, electronics, and power supplies.

The free flow prevention clamp 110 includes a first elongate section 112*a*, a second elongate section 112*b*, and a clamping section 112*c*. The housing of the cassette 102 supports the free flow prevention clamp 110. The clamping section 112*c* is positioned within the cassette geometry such that, when the cassette 102 is received within the receptacle 104 of the ambulatory pump 100, the clamping section 112*c* extends across the channel receiving the tube 108. The housing of the cassette 102 may be rigid plastic or other material capable of supporting the tube 108 and free flow prevention clamp 110.

The first elongate section 112*a* extends from a first side of the clamping section 112*c* and along a first side of the cassette 102 parallel to the channel within the cassette 102 receiving the tube 108. The second elongate section 112*b* extends from a second side of the clamping section 112*c* and along a second side of the cassette 102 parallel to the channel receiving the tube 108. In the illustrated example, the free flow prevention clamp 110 is a staple-shaped leaf spring consisting of single piece of metal (e.g., spring steel). In other examples, the free flow prevention clamp 110 may be formed in pieces and/or of different materials (e.g., the elongate sections 112*a, b* may be metal and the clamping section 112*c* may be rigid plastic).

The ambulatory pump 100 also includes a pair of arc cams (a first arc cam 114*a* on one side of the receptacle is illustrated FIG. 1, with the second hidden from view) for engaging the elongate sections 112*a, b* of the free flow prevention clamp in order to lift the clamping section 112*c*. Additionally, the ambulatory pump 100 includes a pair of wedge cams (a first wedge cam 116*a* on one side of the receptacle 104 is illustrated FIG. 1, with the second hidden from view) for transitioning the free flow prevention clamp 110 from an open, manufactured/shipped state to an operational state, which is described in further detail below.

Figure 3A:
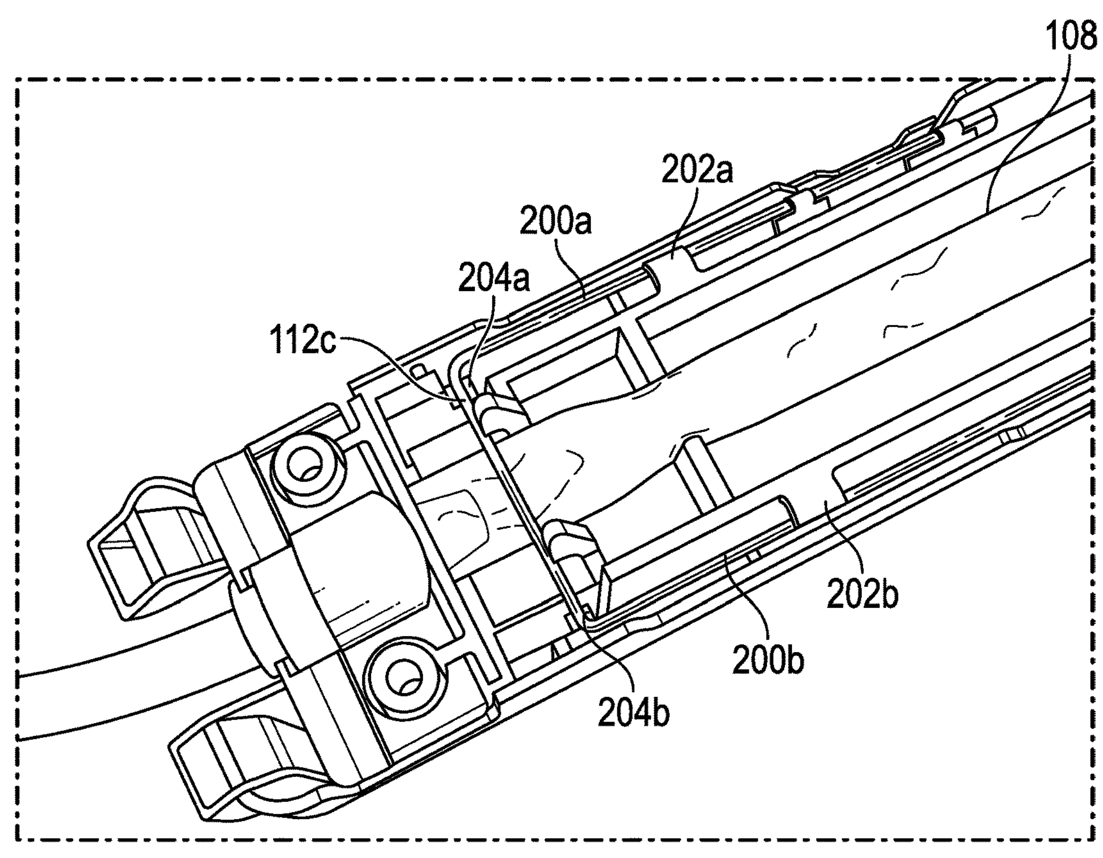
FIG. 3A is a partial perspective view of the cassette of FIG. 2 illustrating the free flow prevention clamp in an open, pre-operational state (e.g., shipped state).

FIG. 3A depicts the cassette 102 with the free flow prevention clamp 110 in an open, pre-operational state (e.g., manufactured/shipped state). The cassette 102 includes at first ledge 204*a* adjacent a first side of the clamping section 112*c* on one side of the channel receiving the tube 108 and a second ledge 204*b* adjacent a second side of the clamping section 112*a* on an opposite side of the channel receiving the tube 108. The ledges 204*a, b* support the clamping section 112*c* and oppose the downward force being applied to the clamping section 112*c* by the first and second elongate sections 112*a, b*. This prevents the clamping section 112*c* from occluding the tube 108 (e.g., for Ethylene Oxide, EtO, sterilization and/or priming) prior to insertion of the cassette 102 into the ambulatory pump 100.

The housing of the cassette 102 additionally includes a pair of override fulcrums 200*a, b* positioned below respective elongate sections 112*a, b* of the free flow prevention clamp 110 and a pair of occlusion fulcrums 202*a, b* positioned above respective elongate sections 112*a, b* of the free flow prevention clamp 110. The override fulcrums 200*a, b* are positioned between a midpoint of the first and second elongate sections 112*a, b* and the clamping section 112*c*. The occlusion fulcrums are positioned between the midpoint of the first and second elongate sections 112*a, b* and the override fulcrums 200*a*.

After the free flow prevention clamp 110 is moved off the ledges 204 and into an operational state, applying a force to the midpoints of the first and second elongate sections 112*a, b* (e.g., by the arc cams 114*a, b* upon attachment of the cassette 102 to the receptacle 104 of the ambulatory pump or by a user's finger) pivots the elongate sections a, b about the override fulcrums 200*a, b* to raise the clamping section 112*c* and allow fluid flow through the tube 108. Removing the force while in this state (e.g., by detaching the cassette or withdrawing the user's finger) shifts the pivot to the occlusion fulcrums 202*a, b*, which lowers the clamping section 112*c* and blocks fluid flow through the tube 108.

Figure 3B:
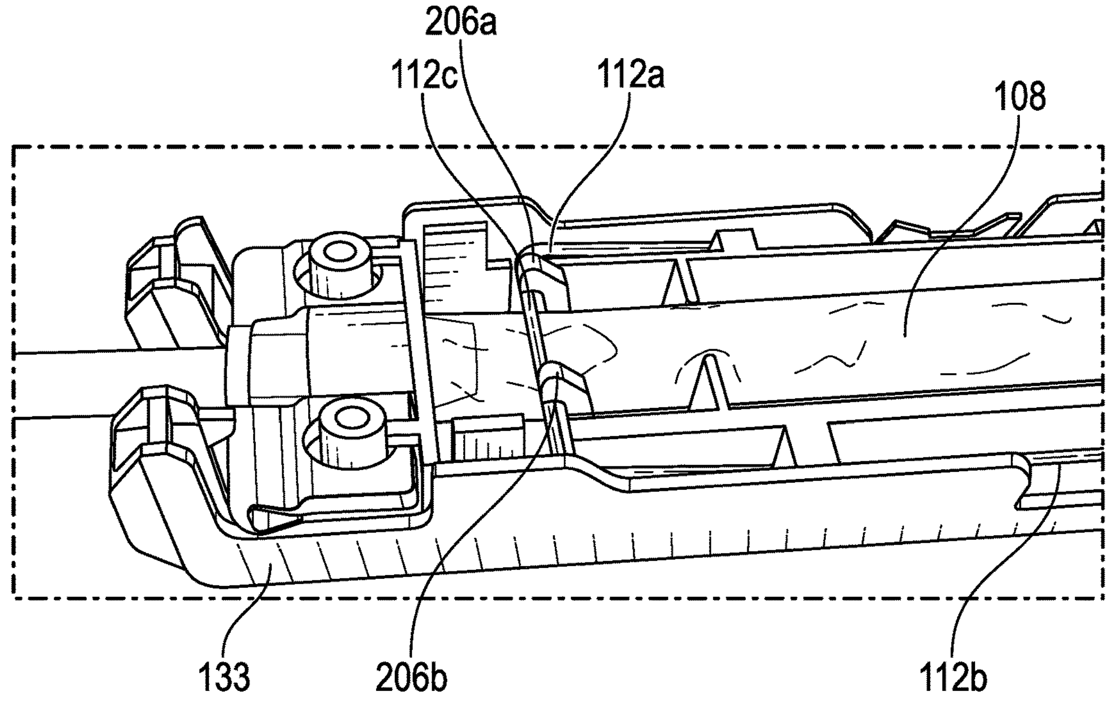
FIG. 3B is a partial perspective view of the cassette of FIG. 2 illustrating the free flow prevention clamp in a closed, post-operational state.
Figure 3C:
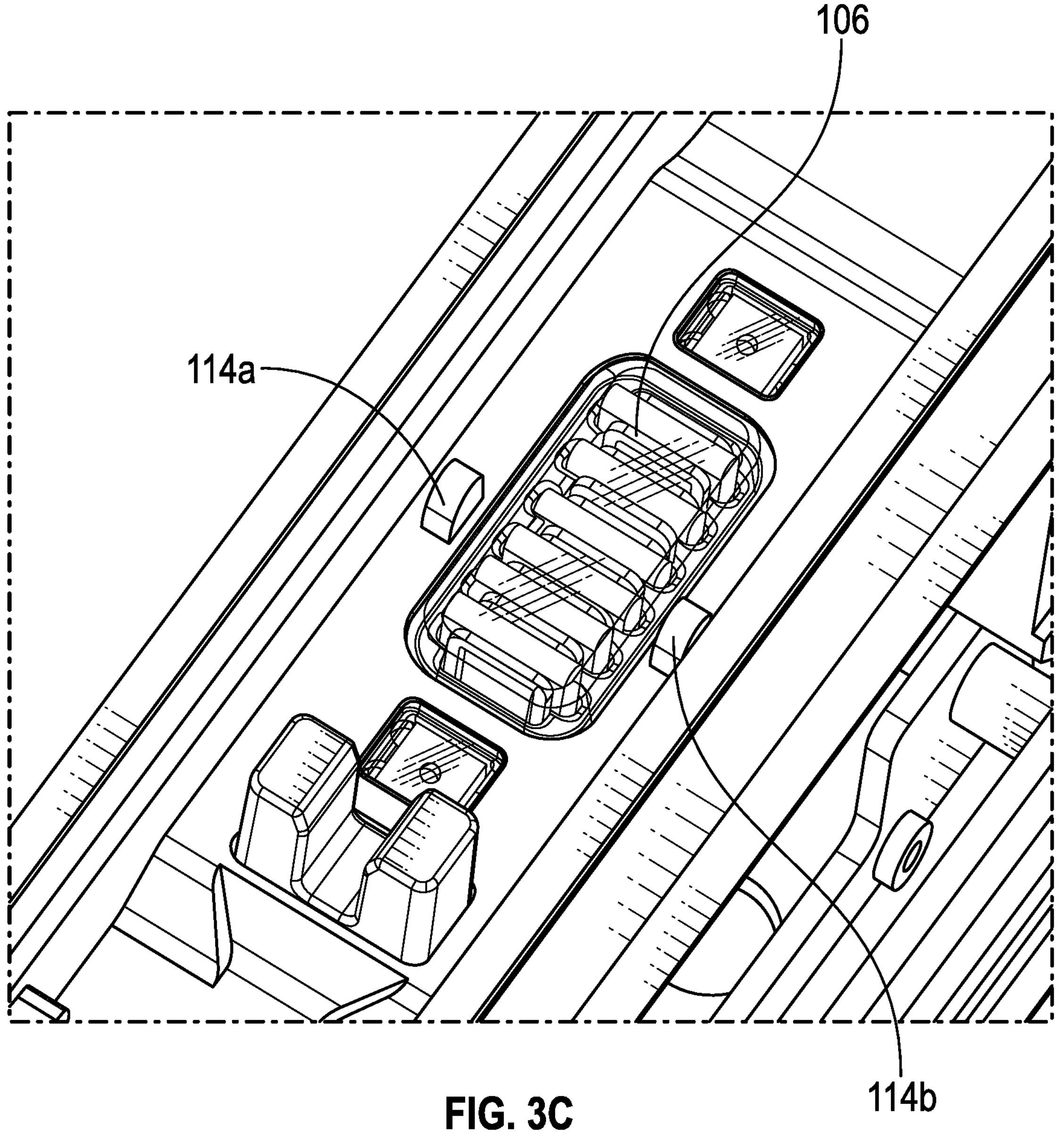
FIG. 3C is a partial perspective view of the pump of FIG. 1 illustrating arc cams that engage the free flow prevention clamp when the cassette is coupled to the pump.
Figure 3D:
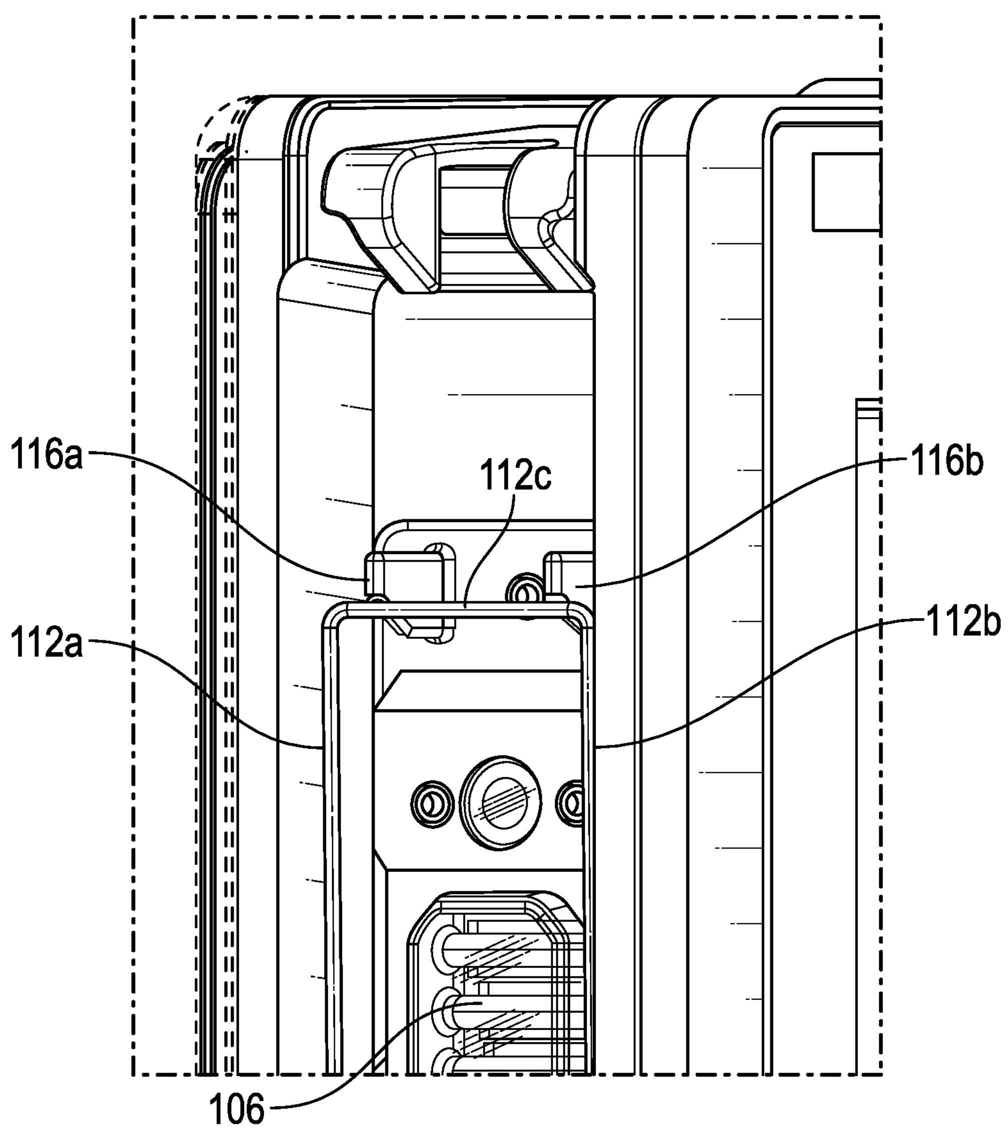
FIG. 3D is a partial perspective view of the pump of FIG. 1 illustrating wedge cams that engage the free flow prevention clamp to shift the free flow prevention clamp from a shipped state to an operational state when the cassette is coupled to the pump.

FIG. 3B depicts the cassette 102 with the free flow prevention clamp 110 in a closed, operational state and FIG. 3C depicts the arc cams 114 and peristaltic pump 106 of the ambulatory pump 100. Guides 206*a, b* are provided to facilitate placement of the clamping section 112*c* of the free flow prevention clamp 110 onto the ledges 204, which maintains the tube 108 in an open condition. FIG. 3D depicts the wedge cams 116*a, b* and their relationship to the free flow prevention clamp when the cassette (not shown in FIG. 3D) is attached to the ambulatory pump 100.

The free flow prevention clamp 110 is moved off the ledges 204 and out of the open, pre-operational state by the wedge cams 116 as the cassette 102 is attached to the receptacle 104 of the ambulatory pump 100. To attach the cassette 102 to the receptacle 104, a user first inserts an end of the cassette 102 adjacent the clamping section 112*c* into the receptacle 104 near a bottom of the ambulatory pump 100. The user then rotates the cassette 102 downward about the toe-in into engagement with the ambulatory pump 100. As the cassette 102 is rotated into position, the arc cams 114 engage the elongate sections 112*a, b* to apply a force that raises the clamping section 112*c* and angled portions of the wedge cams 116 substantially simultaneously engage the clamping section 112*c* to shift the free flow prevention clamp 110 away from the ledges 204. In this manner, the tube 108 remains unobstructed by the clamping section 112*c* when the cassette 102 is attached to the ambulatory pump 100, allowing the peristaltic pump 106 to control fluid flow through the tube 108. In an example, once the free flow prevention clamp 110 is shifted from the shipped/pre-operational state into the operational state by the wedge cams 116, the free flow prevention clamp 110 remains in the operational state.

Removal of the cassette 102 from the receptacle 104 is accomplished by reversing the process. As the cassette 102 is rotated out of engagement with the ambulatory pump 100, the arc cams 114 disengage from the elongate sections 112*a, b*. With the force from the arc cams 114 removed, and the ledges 204 no longer positioned under the clamping section 112*c* due to the shift of the free flow prevention clamp 110 during the insertion of the cassette 102, the clamping section 112 rotates downward about the occlusion fulcrums 202*a* to close off the tube 108 as depicted in FIG. 3B.

Figure 4A:
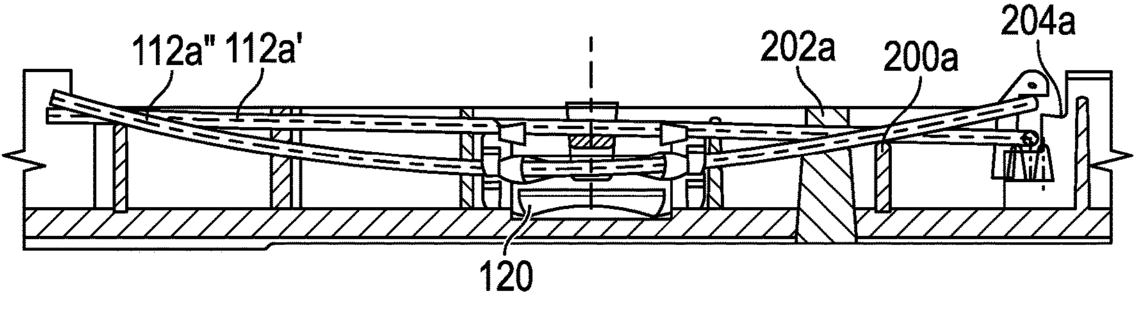
FIG. 4A is a partial side view of the example cassette of FIG. 2 depicting the free flow prevention clamp in an open condition and a closed condition.

FIG. 4A depicts movement of the first elongate section 112 after shifting the free flow prevention clamp 110 off the ledge 204*a* from the open, pre-operational state into the operational state. In the operational state, the first elongate section 112 can be in a closed condition (represented by first elongate section 112') or an open condition (represented by first elongate section 112"). In the closed condition, no force is applied to the midpoint of the first elongate section 112', resulting in the clamping section 112*c* rotating downward about the occlusion fulcrum 202*a* to close off the tube 108. In the open condition, force is applied to the midpoint of the first elongate section 112", resulting in the clamping section 112*c* rotating upward about the override fulcrum 200*a* to open the tube 108.

Figure 4B:
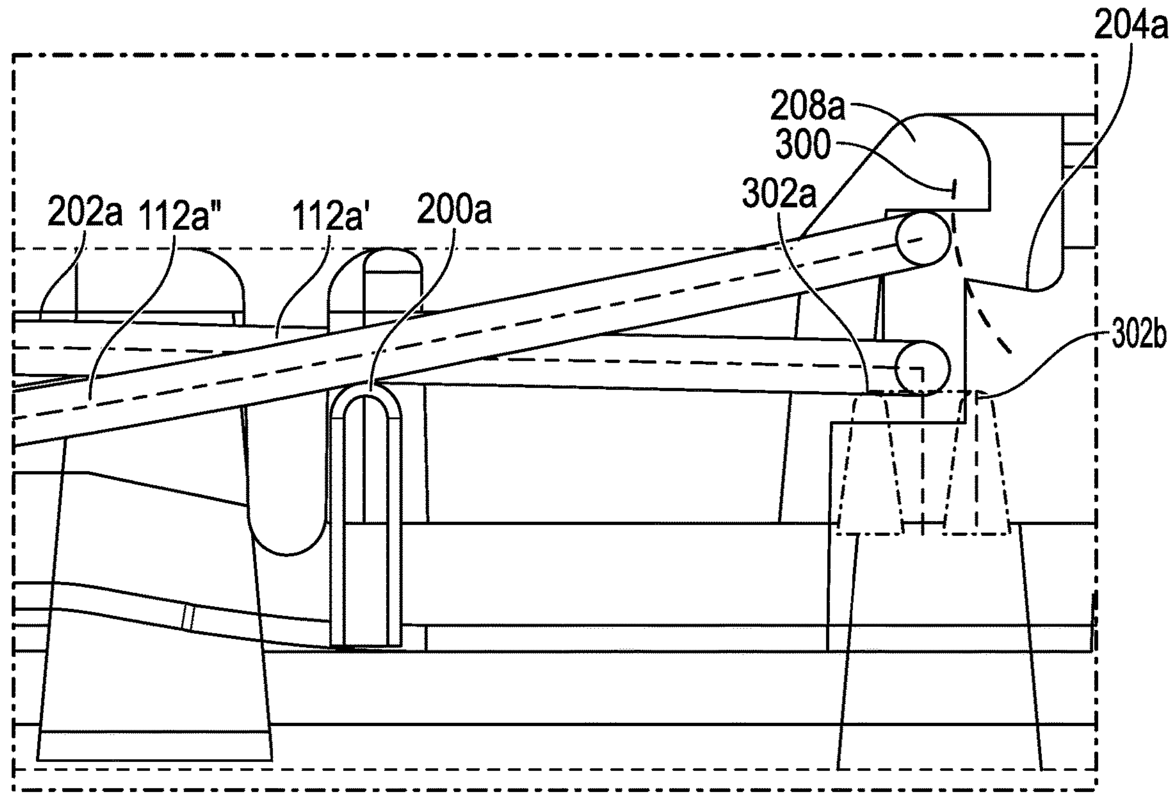
FIG. 4B is a partial side view of the example cassette of FIG. 2 illustrating features of the cassette for configuring the free flow prevention clamp in an open operational state and a closed post-operational state.

FIG. 4B depicts geometry of the housing of the cassette 102 supporting the free flow prevention clamp 110. Shifting of the clamping section 112*c* of the free flow prevention clamp 110 is represented by dashed wedge cam shift line 300. Occlusion fulcrum 202*a* acts on elongate section 112*a*' forcing clamping section 112*c* downward to occlude the tube 108. Occlusion ribs 302*a* and 302*b* are positioned perpendicular to the channel receiving the tube 108 and on either side of the clamping section 112*c* to assist with complete closure of the tube 108 when the clamping section 112*c* is in the closed condition. While occlusion ribs 302*a* and 302*b* are shown in a trapezoidal configuration, they can also be configured as one or more plates, including a single flat plate. Override fulcrum 200*a* acts on elongate section 112*a*" forcing clamping section 112*c* upward to enable fluid flow through the tube 108.

Figure 5A:
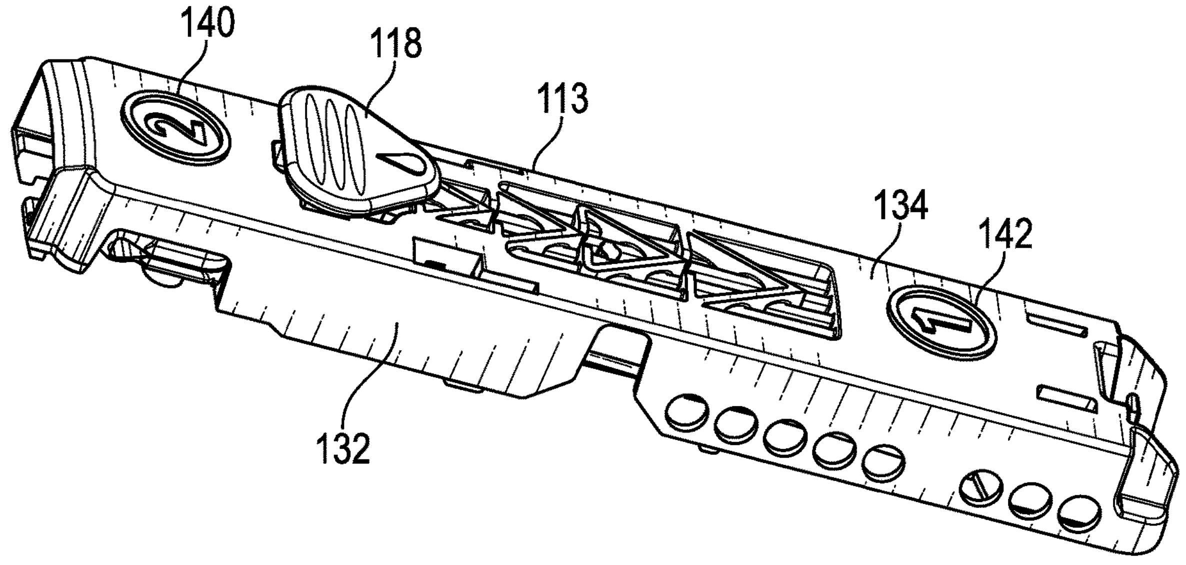
FIG. 5A is a top perspective view of the cassette of FIG. 2 illustrating the free flow prevention clamp showing an actuator assembly according to one example.
Figure 5B:
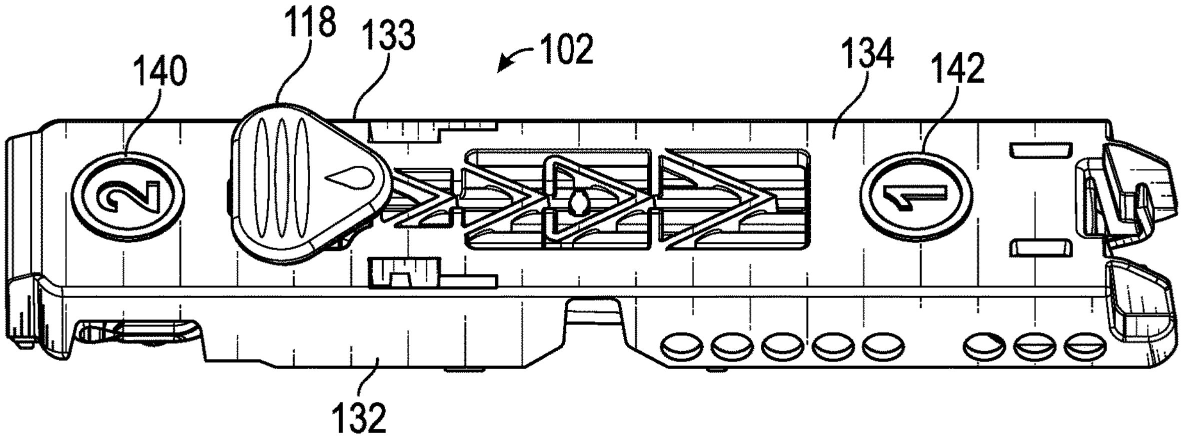
FIG. 5B is a second top perspective view of the cassette of FIG. 2 illustrating the free flow prevention clamp showing an actuator assembly according to one example.

As illustrated in FIGS. 5A and 5B, the cassette 102 include an actuator assembly 117 that includes bypass button 118. The bypass button 118 is positioned on outer surface 134 (user-facing side) of the cassette 102. Bypass button 118 is provided, when pressed, to raise the clamping section 112*c* away from the tube 108 to override the compressive force on the tube 108 exerted by the arms 112*a,b* when the cassette 102 is not in the pump, as described below.

In some examples the bypass button 118 may include tactile features that may allow a user to detect the button without relying on sight. Tactile features include the shape of the button as well as surface indicators. In the illustrated example, the button has a tear-drop shape, which stands in contrast to other structures on the outer surface 134 such as buttons 140, 142, which thereby permits tactile detection. Examples of surface indicators include ridges, grooves, and the like. In other examples, visual indicators may be used. For instance, bypass button 118 may have a noticeable appearance, such as a particular color (surface indicators may also provide such an appearance alone or in combination with color).

Figure 5C:
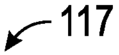
FIG. 5C is a top perspective view of the actuator assembly shown in FIGS. 5A and 5B according to one example.
Figure 5C:
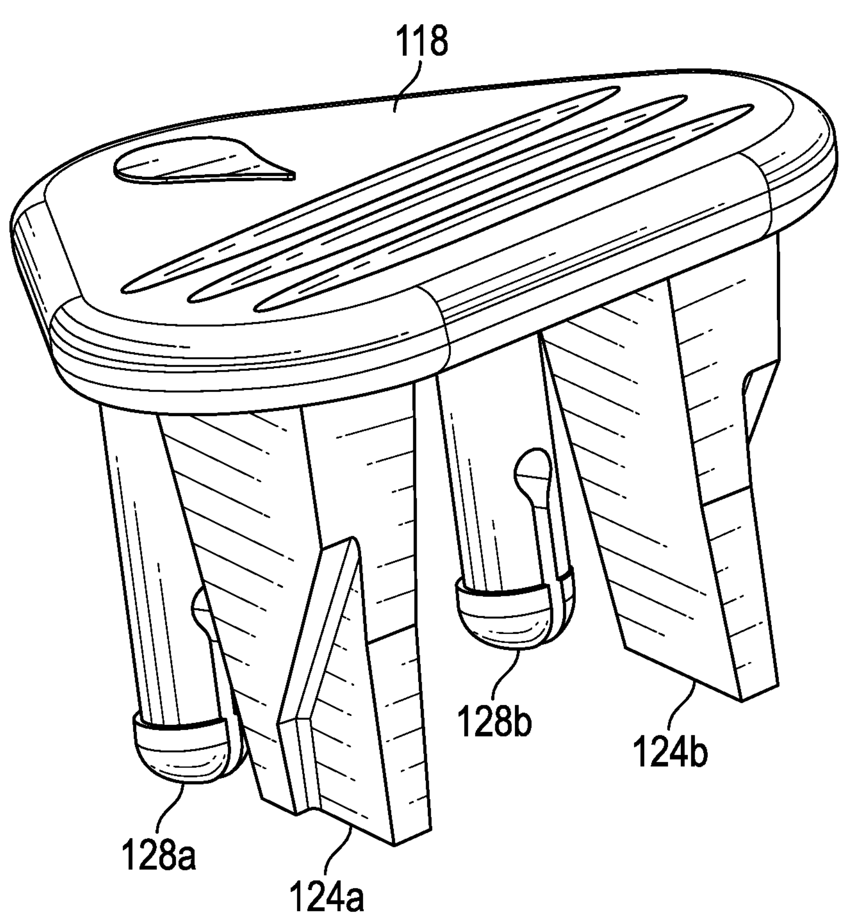
Figure 5D:
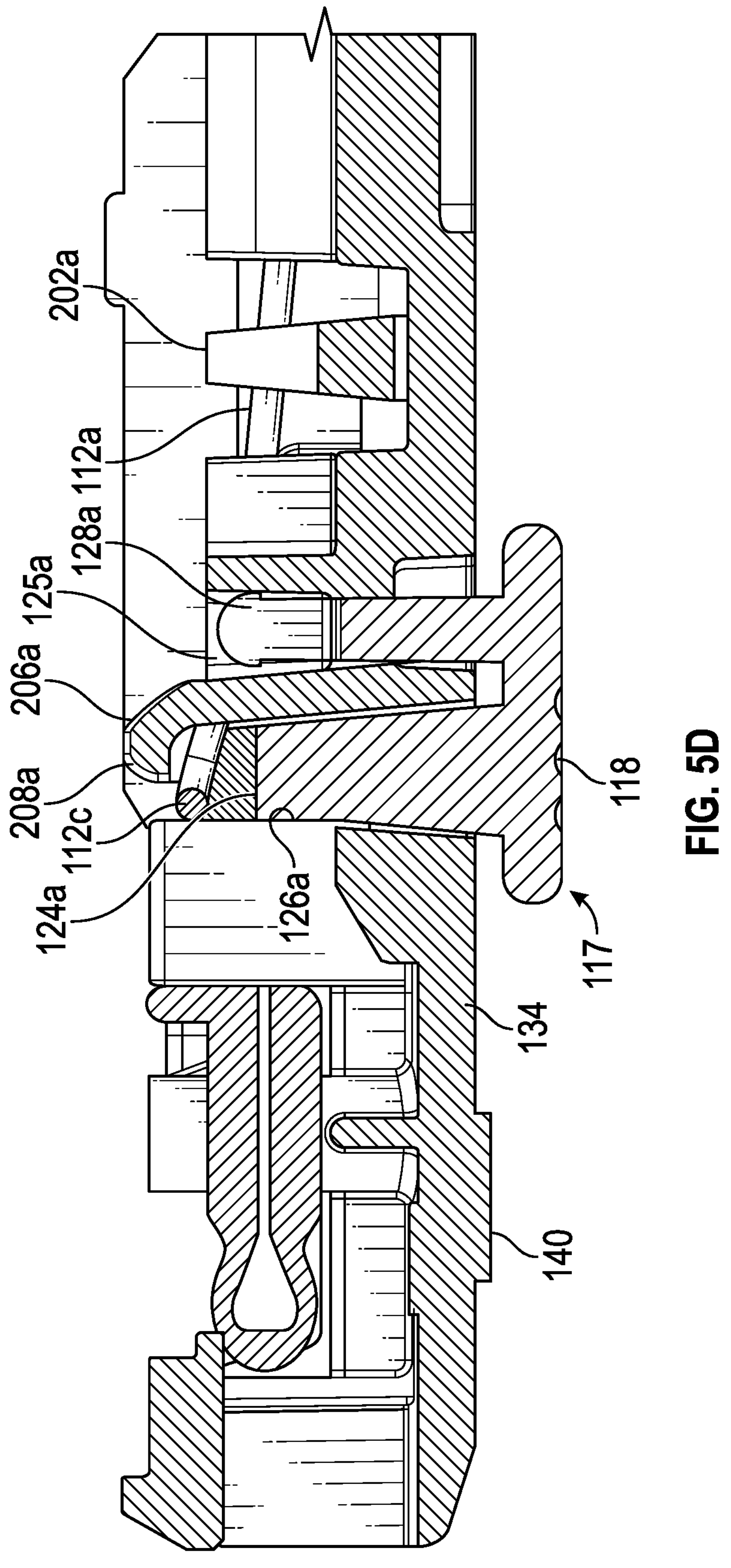
FIG. 5D is a side sectional view of the cassette of FIG. 4A illustrating additional detail of the actuator assembly according to the example.

As illustrated in FIGS. 5C and 5D, the actuator assembly 117 also includes a first pair of legs 124*a,b* (124*b* is not shown) attached to, or formed integral with, bypass button 118 that pass through longitudinal openings, passageways, or holes 126*a,b* in the outer surface of the cassette. The actuator assembly 117 includes at least one pair of spaced apart legs which are configured for slidable engagement into at least one pair of longitudinal openings positioned within the cassette housing 130. At least one leg engages the clamping section 112*c*. In some examples the actuator assembly 117 includes a second pair of spaced apart legs 128*a,b* (126*b* is not shown) that pass through holes 125*a,b* in the outer surface 134 of the cassette to provide additional rigidity and stability. In one example, first (124*a,b*) and second (126*a,b*) pairs of legs and are spaced apart such that legs 124*a*, 126*a* are adjacent to the first side 132 of the cassette and legs 124*b*, 126*b* are adjacent to the second side 133 of the cassette. The legs (124*a,b* and 128*a,b*) of the bypass button 118 are sized so that the first pair of legs 124*a,b* engages but does not lift clamping section 112*c* so that fluid does not flow through the tube 108 without a force exerted upon bypass button 118. Additionally, the legs are sized such that the bypass button 118 is slightly raised from the outer surface 134 of the cassette 102 when there is no force on the bypass button directed towards the outer surface. Guides 206*a,b* are provided to assist in limiting lateral movement of the clamping section 112*c* of the free flow prevention clamp 110. Guides 206*a,b* may additionally include detents 208*a,b* to limit longitudinal movement to complement movement limited by outer surface 134 as described below.

Upon pressing the bypass button 118 towards outer surface 134, with sufficient force to counteract the force applied by the arms 112*a/b* on the clamping section 112*c*, inner portion of the actuator assembly (e.g., legs 124*a,b* and 126*a,b*) extends further into the cassette, moving from a rest position to a bypass position. As the legs extend into the cassette, the first pair of legs drive the clamping section 112*c* off the tube 108 to the bypass position, thereby reducing compression of the tube to permit fluid flow.

Conversely, upon releasing the bypass button, the legs of the bypass button lower the arms 112*a,b* which in turn lower the clamping section 112*c* move back into the normally closed state to prevent fluid flow.

To attach the cassette 102 to the receptacle 104, a user first inserts an end of the cassette 102 adjacent the clamping section 112*c* into the receptacle 104 near a bottom of the ambulatory pump 100. The user then rotates the cassette 102 downward about the toe-in into engagement with the ambulatory pump 100. As the cassette 102 is rotated into position, the arc cams 114 engage the elongate sections 112*a, b* to apply a force that raises the clamping section 112*c* and angled portions of the wedge cams 116 substantially simultaneously engage the clamping section 112*c* to shift the free flow prevention clamp 110 away from the ledges 204. In this manner, the tube 108 remains unobstructed by the clamping section 112*c* when the cassette 102 is attached to the ambulatory pump 100, allowing the peristaltic pump 106 to control fluid flow through the tube 108. In an example, once the free flow prevention clamp 110 is shifted from the shipped/pre-operational state into the operational state by the wedge cams 116, the free flow prevention clamp 110 remains in the operational state.

Removal of the cassette 102 from the receptacle 104 is accomplished by reversing the process. As the cassette 102 is rotated out of engagement with the ambulatory pump 100, the arc cams 114 disengage from the elongate sections 112*a, b*. With the force from the arc cams 114 removed, and the ledges 204 no longer positioned under the clamping section 112*c* due to the shift of the free flow clamp 110 during the insertion of the cassette 102, the clamping section 112 rotates downward about the occlusion fulcrums 202*a* to close off the tube 108 as depicted in FIGS. 3A and 3B.

Examples of the free flow prevention clamp 110 enable the cassette 102 to maintain the clamping section 112*c* in an un-occluded/open state prior to a first attachment of the cassette to the receptacle, maintain the clamping section in the un-occluded/open state upon the first attachment of the cassette to the receptacle, and transition the clamping section to an occluded/closed state upon detachment of the cassette from the receptacle. Additionally, examples of the free flow prevention clamp 110 enable the cassette to manually transition the clamping section to an un-occluded state after detachment of the cassette from the receptacle and/or transition the clamping section to the un-occluded state upon subsequent attachments of the cassette to the receptacle.

The terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. An ambulatory pump system comprising:

a cassette including a free flow prevention clamp, a housing, and an actuator assembly, the free flow prevention clamp including a clamping section having a first side and a second side, a first elongate section extending from the first side, and a second elongate section extending from the second side, the housing supporting the free flow prevention clamp and defining a channel for receiving a tube, the first elongate section and the second elongate section extending parallel to the channel and the clamping section extending across the channel, wherein the free flow prevention clamp is configurable within the housing in an open condition that allows fluid flow through the tube when force is applied to a portion of the clamping section and in a closed condition that prevents fluid flow through the tube when the force is removed from the portion of the clamping section;

the actuator assembly including a portion extending through the housing and configurable for movement between a rest position and a bypass position and a portion extending within the housing configured for contact with the clamping section, wherein upon actuation of the actuator assembly by a user from the rest position to the bypass position, the actuator assembly applies the force to the portion of the clamping section to position the free flow prevention clamp in the open condition; and a pump body including a receptacle configured to receive the cassette, a peristaltic pump positioned adjacent the receptacle to act on the tube when the cassette is received by the receptacle, at least one cam positioned at least partially within the cassette to engage at least one of the first and second elongate sections to apply the force when the cassette is received by the receptacle.

2. The ambulatory pump system of claim 1, wherein the cassette housing further includes at least one ledge adjacent the clamping section, the at least one ledge supports the clamping section in an open, pre-operational state, and the clamping section is moved off the at least one ledge when the cassette is received by the receptacle in the pump body.

3. The ambulatory pump system of claim 1, wherein the actuator assembly includes a portion comprising a button configured for manual actuation by the user.

4. The ambulatory pump system of claim 1, wherein the actuator assembly includes at least one pair of legs, the legs configured for slidable engagement into at least one pair of longitudinal openings positioned within the cassette housing.

5. The ambulatory pump system of claim 1, wherein the cassette is configured to perform the functions of:

maintaining the clamping section in the open condition prior to a first attachment of the cassette to the receptacle; and maintaining the clamping section in the open condition upon the first attachment of the cassette to the receptacle.

6. The ambulatory pump system of claim 1, wherein the cassette is configured to perform the functions of:

transitioning the clamping section to the closed condition upon detachment of the cassette from the receptacle.

7. The ambulatory pump system of claim 6, wherein the cassette is further configured to perform the function of:

manually transitioning the clamping section to the opened condition after detachment of the cassette from the receptacle.

8. The ambulatory pump system of claim 1, wherein the free flow prevention clamp is a leaf spring.

9. A cassette comprising:

a free flow prevention clamp, a housing, and an actuator assembly, the free flow prevention clamp including a clamping section having a first side and a second side, a first elongate section extending from the first side, and a second elongate section extending from the second side, the housing supporting the free flow prevention clamp and defining a channel for receiving a tube, the first elongate section and the second elongate section extending parallel to the channel and the clamping section extending across the channel, wherein the free flow prevention clamp is configurable within the housing in an open condition that allows fluid flow through the tube when force is applied to a portion of the clamping section and in a closed condition that prevents fluid flow through the tube when the force is removed from the portion of the clamping section; and the actuator assembly including a portion extending through the housing and configurable for movement between a rest position and a bypass position and a portion extending within the housing configured for contact with the clamping section, wherein upon actuation by a user of the actuator assembly from the rest position to the bypass position, the actuator assembly applies the force to the portion of the clamping section to position the free flow prevention clamp in the open condition.

10. The cassette of claim 9, wherein the cassette housing further includes at least one ledge adjacent the clamping section, the at least one ledge supports the clamping section in an open, pre-operational state, and the clamping section is moved off the at least one ledge when the cassette is received by a receptacle of a pump body.

11. The cassette of claim 9, wherein the actuator assembly includes a portion comprising a button configured for manual actuation by the user.

12. The cassette of claim 9, wherein the actuator assembly includes at least one pair of legs, the legs configured for slidable engagement into at least one pair of longitudinal openings positioned within the cassette housing.

13. The cassette of claim 9, wherein the cassette is configured to perform the functions of:

maintaining the clamping section in the open condition prior to a first attachment of the cassette to a receptacle of a pump body; and maintaining the clamping section in the open condition upon the first attachment of the cassette to the receptacle.

14. The cassette of claim 9, wherein the cassette is configured to perform the functions of:

transitioning the clamping section to the closed condition upon detachment of the cassette from a receptacle of a pump body.

15. The cassette of claim 14, wherein the cassette is further configured to perform the function of:

manually transitioning the clamping section to the opened condition after detachment of the cassette from the receptacle of the pump body.

16. The cassette of claim 9, wherein the free flow prevention clamp is a leaf spring.

* * * * *